US00PP08326P

United States Patent [19]

Vletter

[11] Patent Number: Plant 8,326

[45] Date of Patent: Jul. 27, 1993

[54] LILY PLANT NAMED OXFORD

[75] Inventor: Floris Vletter, Rijnsburg, Netherlands

[73] Assignee: Gebr. Vletter & J.A., Rijnsburg, Netherlands

[21] Appl. No.: 796,546

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct lily plant named Oxford, characterized by its intense pink flower color with deeper red-purple spots and along the midveins and white edges and tips, very large, upright flowers, and vigorous growth habit.

1 Drawing Sheet

The present invention comprises a new and distinct cultivar of lily, botanically known as Lilium, commercially known as Lilium oriental hybrid, and hereinafter referred to by the cultivar name Oxford. The parents were orientsl varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars having upright flowers, long stems, good color, and other characteristics desirable for cut flower production.

The new cultivar was originated from a hybridization made by the inventor in a controlled breeding program in Rijnsburg, The Netherlands in 1981. The female parent was the cultivar Stargazer, and the male parent was an unnamed seedling.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for Oxford are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Very large flowers which are carried in an upright position.

2. Intense pink flower color, with deeper red-purple spots or markings and along the midvein.

3 The edges and tips of the petals are white.

4. The base area of the petals is a green-yellow.

5. Vigorous growth habit.

Of the many commercial cultivars known to the present inventor, the most similar in comparison to the new cultivar is Stargazer. In comparison to Stargazer, Oxford has fewer spots or markings, longer stems, and vigorous leaves. When flowering is forced under natural light, Oxford produces an inflorescence approximately 12 days earlier than Stargazer, under the same growing conditions. Oxford is fertile.

The accompany photographic drawing shows typical flower characteristics of the new cultivar, with colors being as true as possible with illustrations of this type. The photograph comprises a top perspective view of two open flowers and several buds at various stages.

In the following description, color references are made to The Royal Horticultural Society (R.H.S.) Colour Chart. The color values were determined at Wageningen in 1988–1989 and Rijnsburg in July 1991.

Origin: Seedling from Breeding Program.

Parentage:

*Seed parent.*—Stargazer.

*Pollen parent.*—Unnamed seedling.

Classification:

*Botanical.*—Lilium.

*Commercial.*—Oriental hybrid.

The plant:

*Form.*—A single stem carrying numerous pedicels alternately arranged.

*Height.*—Medium to tall; 105 cm at time of opening of anthers of first flower.

*Growth habit.*—Vigorous.

*Stem.*—Circular in transverse section, internodal length 1.5 cm and uniform; anthocyanin pigmentation in leaf axels.

*Foliage.*—Quantity: 30–40 leaves depending on growing conditions. Size of leaf: Mature leaves are medium in length (15.5 cm), and medium to wide in width (4 cm). Shape of leaves: Generally ovate. Texture: Smooth with weak glossiness; no pubescence. Color: Medium green 137A.

*Bulbs.*—Size: Outlet 6–30 cm. Color: Cream.

*Roots.*—Both stem and contractile present.

The bud:

*Form.*—Tapering (like a lancet).

*Size.*—11.5 cm prior to opening.

*Opening.*—Unfolds normally.
*Color.*—75B.
*Tepals.*—Folded, three visible.

The flower:

*Blooming habit.*—Raceme.
*Size.*—Large, 20 cm in diameter, depending on growing conditions.
*Borne.*—Upright.
*Shape.*—Generally in form of hexagonal star; bowl-shaped in cross-section; tips curved.
*Tepalage.*—Number of tepals: Six. Arrangement: Three inner and three outer; slight marginal undulation; flower more imbricated than normal for liles of this market class. Color: Upper surface: Light purple 62B, with deeper red-purple markings and along midvein; green-yellow near base. Lower surface: White 155D with pink shade. Spotting or marking: Dark pink in color, 1-3 mm in diameter.
*Nectaries and papillae.*—Present; strong.
*Pedicel.*—Length: 5.5 cm. Color: Medium green. Form: Strongly curved.

*Texture.*—Papillose.
*Disease resistance.*—No disease problems noted to date.
*Fragrance.*—Present; medium strong.
*Lasting quality.*—Excellent.

Reproductive organs:

*Stamens, anthers.*—Arrangement: Anthers form a generally circular pattern. Length: Short to medium, 7.5 cm. Number: Six. Filaments: Light green with bend 1 cm below anther.
*Pollen color.*—Light brown to orange brown.
*Anther color*—Purple.
*Pistils.*—One green style; total length of pistil 9.5 cm.
*Stigma.*—Triangular; purple with grey in color.
*Ovaries.*—Triangular in shape; other characteristics typical of oriental lily varieties.

I claim:

1. A new and distinct lily plant named Oxford, as illustrated and described.

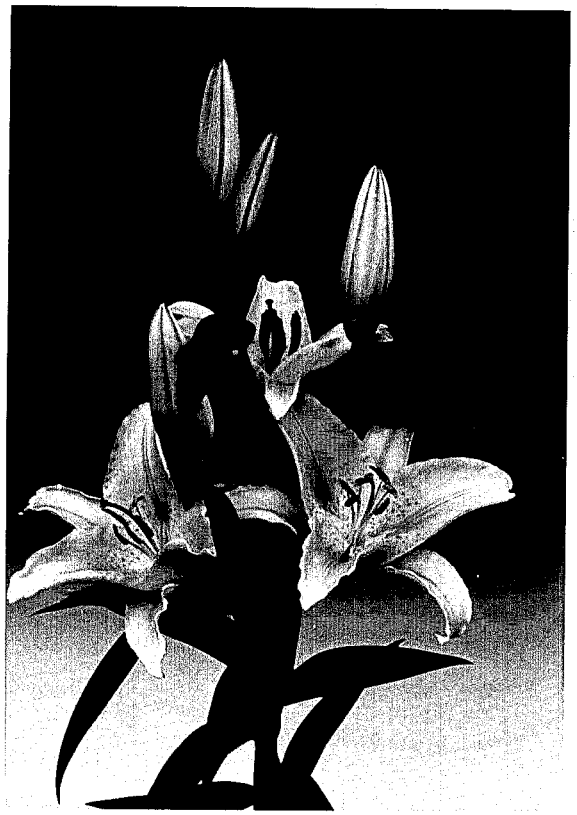

* * * * *